United States Patent [19]

Feizi et al.

[11] Patent Number: 5,122,450
[45] Date of Patent: Jun. 16, 1992

[54] BIOCHEMICAL REAGENT

[75] Inventors: Ten Feizi; Ping W. Tang, both of Harrow, United Kingdom

[73] Assignee: Research Corporation Limited, London, United Kingdom

[21] Appl. No.: 75,744

[22] PCT Filed: Oct. 24, 1986

[86] PCT No.: PCT/GB86/00659

§ 371 Date: Aug. 20, 1987

§ 102(e) Date: Aug. 20, 1987

[87] PCT Pub. No.: WO87/02777

PCT Pub. Date: May 7, 1987

[30] Foreign Application Priority Data

Oct. 24, 1985 [GB] United Kingdom ............... 8526266
Oct. 24, 1985 [GB] United Kingdom ............... 8526267
Oct. 24, 1985 [GB] United Kingdom ............... 8526265

[51] Int. Cl.$^5$ .............. G01N 33/53; G01N 33/543; C01K 15/14; C07H 5/04

[52] U.S. Cl. .................. 435/7.2; 424/450; 427/2; 435/7; 435/177; 435/181; 435/810; 435/814; 436/501; 436/518; 436/527; 436/529; 436/531; 436/530; 436/543; 436/547; 436/808; 436/809; 436/823; 436/824; 530/359; 530/395; 530/403; 530/409; 530/412; 530/811; 530/812; 530/816; 536/18.7

[58] Field of Search ........... 530/395, 359, 812, 816, 530/402, 403, 409, 412, 811; 435/7, 177, 181, 810, 814; 436/501, 518, 527, 528–535, 174, 177, 808, 823, 824, 536, 543, 547, 809, 829, 71; 424/417, 418, 420, 450; 427/2; 536/18.7

[56] References Cited

U.S. PATENT DOCUMENTS

| 3,947,352 | 3/1976 | Cuatrecases et al. | 435/178 |
| 4,419,444 | 12/1983 | Quash | 436/532 |
| 4,831,126 | 5/1989 | Bundle et al. | 435/101 |
| 4,847,080 | 7/1989 | Neurath et al. | 514/12 |
| 4,888,275 | 12/1989 | Holmgren et al. | 436/813 |

FOREIGN PATENT DOCUMENTS

| 0144084 | 6/1985 | European Pat. Off. | |
| 0168159 | 12/1981 | Japan | 436/532 |

OTHER PUBLICATIONS

Gray, Arch. Biochem. Biophys., vol. 163, 1974, pp. 426–428.
Tang et al, Carbohydr. Res., vol. 136, 1985, pp. 259–271.
Tang et al, Biochem. Biophys. Res. Commun., vol. 132(2), pp. 474–480, 1985.
Wood et al, Carbohydr. Res., vol. 90(2), 1981, pp. 269–282.
Wood et al, Arch. Biochem. Biophys., vol. 212(1), 1981, pp. 277–289.
Wood et al, J. Exp. Med., vol. 154, 1981, pp. 432–449.
Wood et al, Arch. Biochem. Biophys., vol. 212(1), 1981, pp. 262–276.

Primary Examiner—Esther L. Kepplinger
Assistant Examiner—Florina B. Hoffer
Attorney, Agent, or Firm—Scully, Scott, Murphy & Presser

[57] ABSTRACT

A biochemical reagent comprises an oligosaccharide, preferably one which has been liberated from an immunogenic glycoprotein or proteoglycan, which is immobilized on a carrier via an intermediate spacer molecule such as a lipid. The lipid molecule should preferably have at least two long lipid tails so that the oligosaccharide is held in spaced relationship to the carrier where is exhibits antibody-binding ability which is almost indistinguishable from that of the original glycoprotein or proteoglycan. The reagent has its application in biochemical testing of oligosaccharides and systems which bind to them.

56 Claims, 2 Drawing Sheets

BIOCHEMICAL REAGENT

This invention relates to a biochemical reagent, its preparation and its uses. More particularly, the reagent of this invention is an immobilised oligosaccharide and has its principal application in the biochemical investigation of oligosaccharides which occur in combination with proteins, as glycoproteins and proteoglycans, and which may be immunologically active.

Production of antibodies by the body is triggered by an encounter between a foreign molecule (an "antigen") and cells of the adaptive immune system. The biochemical mechanisms of antibody production are complex and have not been fully elucidated. What is known is that antigens trigger the immune system to produce antigen-specific antibodies which on subsequent encounters will bind to the antigen resulting in its inactivation. Regions on the antigen to which antibodies bind are known as "antigenic determinants" or, synonymously, "epitopes". In the interests of simplicity, the term "antigenicity" is used herein and in the claims to indicate the ability of a molecule to bind to an antibody.

It is known that when antibodies bind to proteinaceous antigens such as glycoproteins and proteoglycans, the epitope to which the antibody is directed may be a sequence of amino acids on the protein or a sequence of sugar units on one of the glyco group oligosaccharide chains. Investigation of the antigenicity of the oligosaccharides is of significant biochemical and medical interest.

Oligosaccharides, when isolated as such from immunogenic glycoproteins and proteoglycans, do not bind to their known antibodies in vitro; for example, their simple solutions do not bind to antibodies. The probable reason for the absence of antibody-binding ability is that epitopes are only recognised by antibodies when they are presented to the antibodies in specific orientation and concentration.

In Analytical Biochemistry, 139, 168–177, Raja, R. H. et. al. describe a method of bonding oligosaccharides, obtained by enzyme degradation of hyaluronic acid, to immobilising supports to give, for example, affinity chromatography media and polyacrylamide cell culture surfaces. Hyaluronic acid is a polysaccharide, occurring in connective tissue, with a molecular weight of several million and composed of repeating units of N-acetylglucosamine and glucuronic acid. Partial digestion of hyaluronic acid with the enzyme hyaluronidase, under the conditions descibed by Raja, produces a mixture of fragments of which about fifty percent have an average size of from six to eight disaccharide units (i.e. from twelve to sixteen monosaccharide units). This oligosaccharide mixture is bonded to the immobilising support by a method which involves the following sequential steps: (a) reduction of the oligosaccharide with sodium borohydride, which results in cleavage of the terminal sugar ring and formation of a methylol group at the site of the ring opening, (b) selective oxidation of the methylol group with sodium periodate to form an aldehyde group, (c) coupling of the aldehydo-oligosaccharide to an alpha, omega alkyldiamine such as hexane diamine in the presence of sodium cyanoborohydride resulting in a derivative which has the oligosaccharide residue at one end of a polymethylene chain and an active amino group at the remote terminus (omega postion); and, (d) bonding of the derivatized oligosaccharide, via the omega amino group, to a chromatography support, such as Sepharose (Trade Mark), under the action of cyanogen bromide or, alternatively, to a polyacrylamide cell culture surface under the action of sodium cyanoborohydride.

It is known that reducing disaccharides (i.e. those having active aldehyde groups) may be coupled to proteins or to aminoethyl polyacrylamide gels by selective reduction of a Schiff base, formed between the reducing (aldehyde) group of the disaccharide and the amino group of the protein or the aminoethyl gel using sodium cyanoborohydride [Gray, G. R. (1974), Arch. Biochem. Biophys.; 163, 426–428]. It is the reductive animation method of Gray which is utilised by Wood and Kabat to produce conjugates of isomaltosyl oligosaccharides with lipids [J. Exp. Med., 154, 432–449, (1981)]. In Wood and Kabat's immunological study of isomaltosyl oligosaccharides, the oligosaccharides are conjugated to stearylamine (octadecylamine). The stearyl isomaltosyl oligosaccharide conjugate was found to trigger production of immunoglobulins (i.e. the conjugate was immunogenic) when injected into test rabbits, provided it was first emulsified with complete Freund's adjuvant (CFA) in which, it is said, the conjugate forms miscelles. The conjugate was also found to induce antibody production in rabbits when it was incorporated into liposomes. It is reported that the larger oligosaccharides are rather more active than the shorter, the suggestion being that the shorter chains do not protrude sufficiently from the liposome surface to be active.

An object of the present invention is to enable the analysis of the interaction of oligosaccharides and molecules to which they bind by providing materials and methods directed to this end.

According to the present invention there is provided a biochemical reagent comprising an antigenic conjugate between an oligosaccharide and an immobilising carrier, said oligosaccharide being bound in spaced relationship to the carrier by means of an interposed non-antigenic spacer molecule whereby the oligosaccharide is presented in antigenically active steric configuration for binding on encountering its antibody.

The term "antibody" is used herein is to be construed as including all carbohydrate-binding moieties.

The invention also provides a method for the screening of antibodies which comprises contacting a solution containing an antibody with the immobilised antigenically active conjugate aforesaid and thereafter detecting the occurrence (or non-occurrence) of binding.

The spacer molecule is preferably a lipid molecule and, more preferably, a glyceride or phosphatide which possesses at least two hydrophobic polyalkylene chains. The combination of the oligosaccharide and the lipid is hereafter referred to as a "neoglycolipid".

The spacer molecule may be a long chain fatty acid of from 5 to 50, preferably 5 to 30 and more preferably 10 to 25, carbon atom length, an example being stearylamine and similar amino derivatives of lauric, myristic and palmitic acids. Simple amino hydrocarbons may also be employed. The amino group is necessary for chemical bonding to the oligosaccharide to form the antigenic conjugate.

Neoglycolipids may be formed by reacting an oligosaccharide having at least one aldehyde group with an amine having one or more hydrophobic groups.

Preferably the neoglycolipid has the following formula:

where
R¹ represents a carbohydrate group,
R² represents an alkyl, or alkoyl group,
R³ represents an alkyl, or alkoyl group,
R⁴ represents an alkyl, or alkoyl group, or hydrogen
R², R³ and R⁴ being the same or different groups, z is zero or 1,2 or 3 and X represents a linking group which may be selected from:

Neoglycolipids of particular interest, have the general formula:

where the integers n, and m have a value within the range 5 to 50, preferably 5 to 30, and desirably 10 to 25.

The carbohydrate group R¹ may be derived from a monosaccharide, oligosaccharide, or even a polysaccharide which contains an aldehyde group. A carbohydrate group R¹, which does not in itself contain the necessary aldehyde group, may be subjected to oxidation, for example using periodate oxidation. Of particular biochemical interest are carbohydrate groups which can be isolated from glycoproteins and proteoglycans by a reduction treatment resulting in a reduced oligosaccharide which contains a methylol group, in which case, to form the necessary aldehyde they may be subjected to a periodate oxidation treatment as described by Raja et al, in Anal. Biochem, 1984, Vol 139, pages 168–177.

The most preferred spacer compounds are represented by phosphatidyl ethanolamine dipalmitoyl (PPEADP) and its analogues, L-alpha-phosphatidyl-L-serine, L-alpha-phosphatidyl-ethanolamine (PPEA) dilauroyl, PPEA dimyristoyl, PPEA distearoyl, PPEA beta-oleoyl-gamma-palmitoyl.

The immobilising carrier may be a plate of plastics material such as polyvinyl chloride, a chromatographic support material such as silica gel or a liposome.

In preferred embodiments of the invention the oligosaccharide is obtained from a naturally-occurring glycoprotein or proteoglycan.

Oligosaccharides may be bound to proteins via an oxygen atom (O-linked) or via a nitrogen atom (N-linked). Two different approaches are necessary for the liberation of the oligosaccharides from their bound protein by chemical means. Treatment with alkaline sodium borohydride will break the O-link and simultaneously open the terminal saccharide ring with formation of a methylol group at the ring cleavage site (Iyer and Carlson, Arch. Biochem. Biophys., 1971, Vol 142, pages 101 to 105). Similarly, N-linked oligosaccharides may be obtained and purified in the reduced state (Fukuda et al J Biochem. 1976, Vol 80 pages 1223–1232 and Takasaki et al. Methods Enzymol 1982, vol 83, pages 263–268) and suffer from the limitation described above in that, being fully reduced they are not reactive per se and require oxidation to introduce an aldehyde group. Alternatively, the oligosaccharides may be liberated from their bound protein by enzyme action.

Figure 1:
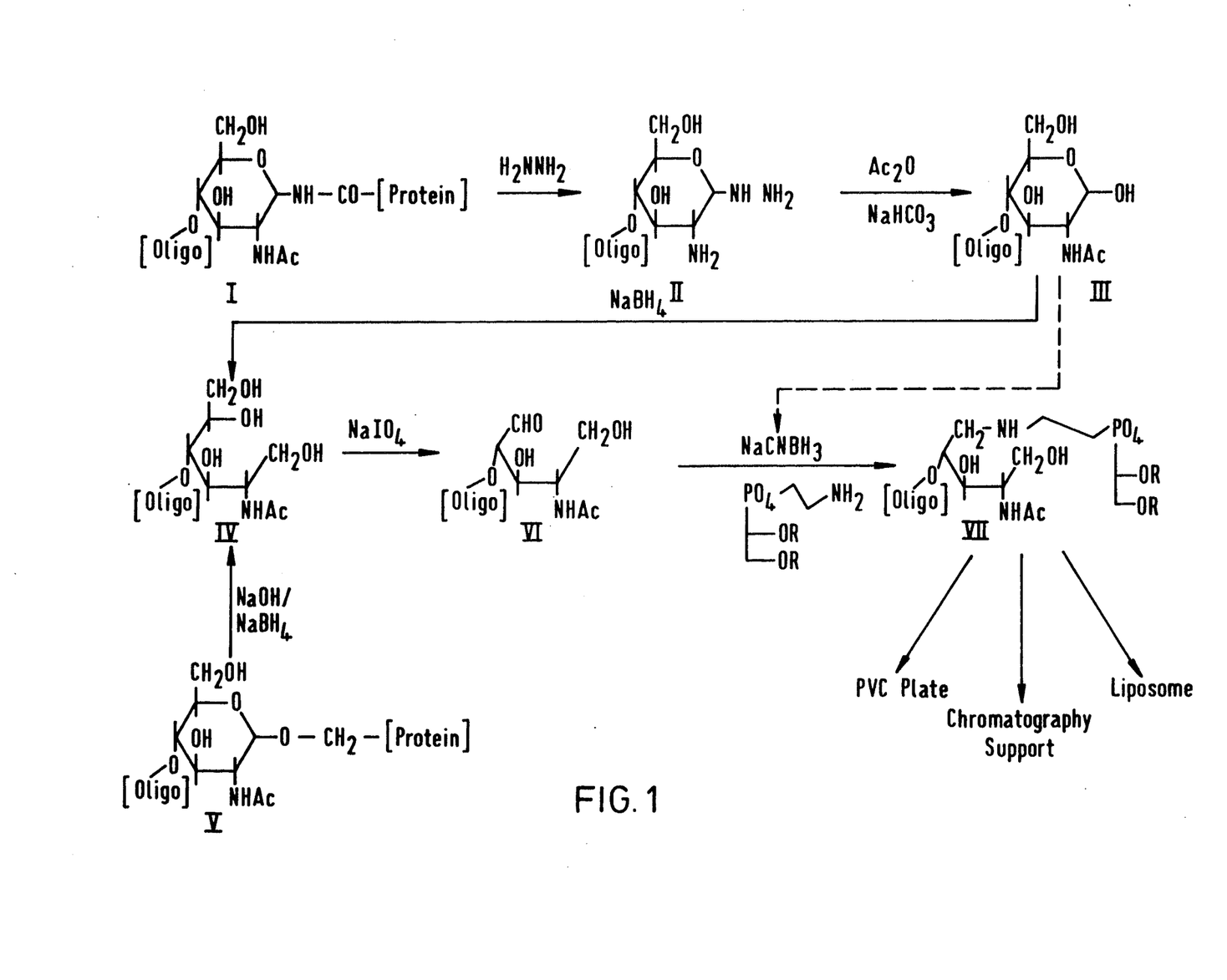

Reference is made to FIG. 1 of the accompanying drawings, which shows a reaction scheme for the liberation of O- and N-linked oligosaccharides from glycoproteins and proteoglycans and their reaction with lipids to form neoglycolipids. The pyranose ring structure shown in FIG. 1 is shown as N-acetylglucosamine for the purpose of illustration only and is to be construed as representative of a terminal saccharide ring of any oligosaccharide, the remainder of the oligosaccharide molecule being represented by the symbol [Oligo].

An N-linked protein bound oligosaccharide (structure I) is subjected to hydrazinolysis which breaks the linkage between the saccharide and its bound protein (represented by [Protein]) with formation of an hydrazido group at the site of the original saccharide/-protein link (structure II).

Acetylation with acetic anhydride and neutralisation converts the hydrazido group to a hydroxyl group and re-N-acetylates the amino group (structure III).

Treatment of the hydroxy compound shown in structure III with sodium borohydride cleaves the terminal saccharide ring structure with formation of a methylol group (—CH₂OH) at the site of ring cleavage (structure IV).

An oligosaccharide bound to a protein via an O-link (structure V) is treated with sodium hydroxide/sodium borohydride which cleaves the terminal saccharide ring with formation of a methylol group at the cleavage site (structure IV).

The methylol compound shown as structure IV is fully reduced and is unreactive with amines. Selective oxidation of the methylol group using sodium periodate under strictly controlled conditions, of which details will be given hereinafter, results in the reducing (aldehydo) oligosaccharide shown as structure VI.

The reducing oligosaccharide (structure VI) is reacted with an lipid amine such as is represented by the phosphatide indicated in FIG. 1, in the presence of sodium cyanoborohydride to give the neoglycolipid (structure VII). The R groups of the phosphatide are as hereinbefore described.

It is possible to react the sugar alcohol, shown as structure III, directly with the cyanoborohydride and lipid to obtain the neoglycolipid VII but this route (indicated by the broken line in FIG. 1), although removing several steps of the multi-step reaction scheme, results in a product which may contain isomeric forms of the neoglycolipid and its utility is thus reduced.

Therefore, according to the present invention, there is provided a method for preparing a biochemical reagent comprising liberating an oligosaccharide moiety of an immunogenic glycoprotein or a proteoglycan under reduction conditions to form thereby a reduced oligosaccharide, selectively oxidising the reduced oligosaccharide with periodic acid or a salt thereof to form an aldehydooligosaccharide, and conjugating the aldehydooligosaccharide with an immobilising carrier via a spacer molecule containing an amino group.

While not wishing to be bound by this particular theory, the following is given by way of explanation of the invention. It is known that when antibodies are generated in vivo in response to glycoprotein and proteoglycan immunogens they often display specificity for epitopes on the oligosaccharides which make up the glyco group. The binding of antibodies is a stereospecific mechanism which depends on the ability of an antibody to recognise a complementary molecular configuration on an epitope. Both of the short arms (Fab) of the antibody seek epitopes and bind thereto and so it is evident that correct three-dimensional presentation of the epitopes with respect to orientation and spacing between pairs of epitopes, and with respect to the physical separation of each epitope from the carrier matrix is essential to ensure efficient and stable binding of the antibody via both of its arms. It is probable, then, that regeneration of the antigenicity of oligosaccharides released from glycoproteins and proteoglycans requires that the epitopes be presented in a sterospecific configuration and, it may be postulated, in a manner which allows some molecular flexibility to enable the antibody arms to locate two epitopes and draw them into the required lateral displacement. Oligosaccharides appear to lose their antigenicity when released from glycoproteins and proteoglycans, i.e. they are in the free state, nor are short chain oligosaccharides rendered antigenic by mere direct binding to an immobilising carrier. When bound to a carrier via short chain spacer molecules the antigenicity of short chain oligosaccharides is present but may be weak. Long chain oligosaccharides do display some weak antigenicity when bound to a carrier via short chain spacer molecules. There does, therefore, appear to be some relationship between antigenicity and the spacing between the epitope and the surface of the carrier. The antigenicity of the conjugate of the invention may be optimised by experimentation with spacer molecules of various chain lengths. However, in practical terms, the oligosaccharides of biochemical interest have normally no more than about seven or eight sugar units and for molecules of this size spacers with twelve to eighteen carbon chains allow the epitope of the sugars to be presented antigenically. The second feature which is thought to participate in the binding mechanism is the lateral spacing between the epitopes. It is well known that the hydrophobic tails of lipid molecules tend to aggregate in solution. It has been found that antigenicity can be optimised by using lipid spacer molecules which have at least two hydrophobic lipid tails. This is believed to induce localised clustering of the tails on the carrier which should affect the lateral spacing of the epitopes at the remote end of the lipid-/oligosaccharide conjugate. This postulate is supported by the observation that double-tailed conjugates have greater antigenicity than single-tailed conjugates of the same oligosaccharide, presumably because of an enhanced clustering effect induced by the multiple hydrophobic tails.

This invention also relates to a method for evaluating the antigenicities and/or receptor functions of oligosaccharides released from glycoproteins and proteoglycans.

There is an increasing awareness of the importance of carbohydrate chains of glycoproteins and proteoglycans of animal cells as onco-developmental antigens recognised by monoclonal antibodies, and as receptors for infective agents as well as endogenous ligands. Consequently there is a need for a micromethod for evaluating the antigenicities and/or receptor functions of oligosaccharides released from the peptide moieties of glycoproteins or proteoglycans by the methods described above. Although several hundreds of milligrams of immunogenic proteins may be available as starting material, the amount of individual purified oligosaccharides, released from the glycoproteins, is very small.

The method of this invention may be performed using minute amounts of oligosaccharides by converting them into neoglycolipids prior to assay.

Therefore, according to one aspect of the present invention there is provided a micromethod for evaluating the antigenicities and/or receptor functions of an oligosaccharide comprising, (a) reacting a reducing oligosaccharide with an amine spacer molecule having the formula where $R^1$ represents an alkyl or alkoyl group, $R^2$ represents an alkyl or alkoyl group or hydrogen, $R^3$ represents an alkyl or alkoyl group or hydrogen, $R^1$, $R^2$ and $R^3$ being the same or different, and X represents a linking group to form a neoglycolipid, (b) conjugating the neoglycolipid on to an immobilising carrier; and, (c) contacting the conjugate with an antibody or other carbohydrate binding system and observing the occurrence (or non-occurrence) of binding of the conjugate.

Preferably the said micromethod includes the step of liberating protein-bound oligosaccharide from the protein and selectively oxidising the oligosaccharide with a salt of periodic acid under controlled conditions to form a reactive reducing oligosaccharide.

Particularly preferred spacer molecules are the derivatives where the R groups are alkoyl groups derived from the fatty acids lauric, myristic, palmitic and stearic acids. Longer or shorter chain lengths may be appropriate in particular circumstances but chains of 12 to 18 carbon atoms are appropriate for most purposes, being a compromise between the shorter chains which may only produce antigenicity with longer chain oligosaccharides, and longer chain spacer molecules which impart no significant enhancement of the antigenicity and which are not readily available. As will be later illustrated in the Examples, it is apparent that there is a correlation between the chain length of the spacer and the induction of antigenicity.

The extent of binding of the conjugated oligosaccharide of the invention with an antibody may be determined by any of the well known methods. For example, radioactively labelled antibodies or carbohydrate receptor system may be used and the amount bound to the oligosaccharide detected by means of the radioactive label. Where unlabelled antibodies are bound, radiolabelled secondary antibodies specific to the relevant class of unlabelled antibody (e.g. anti-mouse IgG antibody) may be added, and after incubation the degree of radioactivity measured.

Especially when the neoglycolipids are derived from PPEADP, their antigenic activity is virtually indistinguishable from its activity on the glycoprotein or proteoglycan from which the oligosaccharide is isolated. Thus the conjugate of the invention enables the oligosaccharide moiety to:

(a) be recognised by antibodies or carbohydrate binding systems, or (b) compete with other molecules having antibody or carbohydrate binding activity.

Thus the test method may be used for characterising physiological status, or for the typing of tissues, cells or infective agents.

An alternative assay enables the identification of oligosaccharides by contacting same with an immobilised antibody so that oligosaccharides containing an epitope recognised by the antibody will be bound to the immobilised antibody thereby confirming its identity.

In general, the assay method of the invention enables the study of the interaction between specific oligosaccharide structures and antibodies. It therefore provides a valuable tool for:

1. basic research, for characterising antibodies;
2. basic research, for characterising oligosaccharide structures, that is, using specific antibodies as structural reagents;
3. diagnosis, for measurement of quantitative or qualitative changes in oligosaccharides or antibodies;
4. purification of antibodies; and
5. therapy.

The following are specific examples of the assay procedures which may be performed using the reagent of this invention:

I DETERMINATION OF ANTIBODY BINDING CHARACTERISTICS

Oligosaccharides are immobilised in a conjugate of the invention and the binding of antibodies thereto are measured. The oligosaccharides may be homogeneous or derived from a particular immunogenic glycoprotein or proteoglycan, cell fraction, cell, tissue or body fluid. For example, the assay method of the invention may in particular be used to diagnose the nature or status of a disease in a living organism. This may be achieved for example when antibodies with specific oligosaccharide-binding characteristics are produced in the organism as a result of a disease state, and are hence diagnostic for that state. In this procedure, antibodies would be isolated from, for example, plasma, and their specificity determined by performing binding assays to conjugates of the invention which contain a range of oligosaccharides.

II DETERMINATION OF THE CHARACTERISTICS OF OLIGOSACCHARIDES

Using the procedure described in paragraph I, specific antibody/conjugate complexes are selected. Then a test preparation of conjugate, in which the carrier is a liposome and the identity of the oligosaccharide is unknown, is allowed to compete with plate-bonded conjugate for the bound antibody. Removal of the antibody by the test antigen indicates the similarity between the structures of plate-bound and liposome-bound oligosaccharides. This procedure allows characterisation of oligosaccharides and typing of cells according to their oligosaccharide-binding ability.

III DETERMINATION OF THE CHARACTERISTICS OF CELLS AND MICROORGANISMS

A conjugate containing a specific oligosaccharide is bound to a PVC plate and cells or microorganisms are tested directly for their ability to bind to the plate. This method enables the typing of cells or strains of microorganisms.

IV ISOLATION OF ANTIBODIES

By passing a solution of antibodies over a conjugate of this invention containing an oligosaccharide of interest, the antibody to the oligosaccharide will bind, allowing the remainder to be washed away and the linked antibody thereafter released in purified form.

V EFFECTOR FUNCTION

A conjugate of the invention may be administered in vivo to produce an immune response, for example, as an antagonist, the conjugate may compete with the oligosaccharides on the surface of infective microorganisms for binding sites on receptor cells, and vice versa, thus preventing infection. Also, it can be used to produce an immune response as an agonist or antagonist to modify the function of glycoprotein hormones or glycoprotein receptors whose functions are mediated by carbohydrate structures.

The invention will now be described, by way of illustration in the following Examples.

EXAMPLE 1

Thin Layer Chromatography

The following experiments were conducted to illustrate the binding of the neoglycolipid to silica gel and to elucidate the relationship between the chain lengths of the spacer molecule and the oligosaccharide. At the same time optimum conditions for the binding were investigated.

Eight different amines as spacer molecules were investigated in three experiments. Oligosaccharides were chromatographed on high performance silica gel TLC plates using standard methods and the plates were then oxidized with periodate followed by reaction with the amine and sodium cyanoborohydride to bind the oligosaccharide fractions to the plate.

The method employed for the periodate oxidation was as follows:

1. From 3 to 5 micrograms of the oligosaccharide are applied to appropriate lanes of a HP-TLC plate.
2. The chromatogram is developed in an appropriate solvent system, for example butan-1-ol:acetone:water 6:5:4 by volume, and the plate then dried and cut into lanes.
3. A solution of 0.02% of sodium periodate in a mixture of 40 mM imidazole hydrochloride (pH 6.5):chloroform:methanol 1:5:5 by volume is prepared, cooled to 4° C. and stored in the dark.
4. Each lane of the TLC is immersed in the periodate solution for ten seconds. The organic solvent is allowed to evaporate in air for a few seconds.
5. The strips are immediately placed in a humid box at 4° C. in the dark and maintained therein for 45 minutes.

6. Each lane is then immersed in a 0.5% w/v solution of the coupling amine (usually PPEADP) in chloroform:methanol 1:1 v/v for ten seconds
7. The lanes are then placed in an air oven at 60° C. for a period of one hour.
8. Each lane is then immersed into a 0.2% w/v solution of sodium cyanoborohydride in chloroform:methanol 1:1 for ten seconds.
9. The lanes are replaced in the 60° C. air oven for a further two hours.

It was the protocol described above which was employed in all the chromatograms discussed in this Example, various amines being employed to determine the extent of the binding and the antigenicities of the various amines as spacer molecule for the conjugates.

In addition, a further test was undertaken to investigate the influence of the periodate oxidation step on the binding properties of the conjugate. Dextran hydrolysate was used as the test oligosaccharide which was oxidised with periodate by the protocol described, the concentration of the periodate was varied to attempt to ascertain an optimum value. The chromatogram was stained with orcinol and then washed. The density of the stained bands was assessed.

As a result of this test it was found that the lower limit for periodate concentration was 0.005% and the upper 0.05% with the optimum at 0.02% which was confirmed in the practical use of the invention in TLC binding assays.

The results are tabulated below in Tables I to III. In the experiments leading to the results shown in Tables I and II, the conjugated oligosaccharides were exposed to anti-Ma antibody or anti-5D4 antibody followed by a radiolabelled second antibody then washed and autoradiographed. The results presented in Table III were produced by direct orcinol staining of the oligosaccharide moiety of the conjugate to determine the level of binding to the TLC plate. An assessment of the density of the bands was made (on a scale of 0 to 1, the maximum being indicated by 1), giving an indication of the binding efficiency.

Table I shows the effect of using various spacer amines on the antigenicities of a trisaccharide. Table II gives the results using a dodeca-saccharide, and, the data in Table III demonstrates the level of binding to TLC plates of a mixture of oligosaccharides derived from dextran hydrolysate, as a function of the type of spacer molecule.

TABLE I

| Immunostaining of trisaccharide v Ma antibody | |
|---|---|
| AMINE | DENSITY |
| PPEA dimyristoyl | 1.0 |
| PPEA distearoyl | 1.0 |
| PPEADP | 1.0 |
| PPEA oleoyl palmitoyl | 0.5 |
| PPEA dilauroyl | 0.1 |
| Sphingosine | not detectable |
| Stearylamine | not detectable |
| PPS | not detectable |

TABLE II

| Immunostaining of J1 Dodecasaccharide v D4 Antibody | |
|---|---|
| AMINE | DENSITY |
| PPEA dimyristoyl | 1.0 |
| PPEADP | 0.9 |
| PPEA distearoyl | 0.8 |
| PPEA oleoyl palmitoyl | 0.5 |
| PPS | 0.5 |
| Stearylamine | 0.2 |
| PPEA dilauroyl | 0.2 |
| Sphingosine | trace |

TABLE III

| REDUCED DEXTRAN HYDROLYSATE with ORCINOL STAIN | |
|---|---|
| AMINE | DENSITY |
| PPEA dilauroyl | 1.0 |
| Stearylamine | 0.8 |
| PPEA dimyristoyl | 0.8 |
| PPEAD oleoyl palmitoyl | 0.8 |
| PPS | 0.5 |
| PPEA distearoyl | 0.5 |
| PPEADP | 0.5 |
| Sphingosine | 0.2 |

The various amines used in generating the data given in Tables 1 to 3 are characterised as follows:

| AMINE | M.W. | NOTES |
|---|---|---|
| L-alpha-phosphatidyl-L-serine (PPS) | 313 | no lipid tail |
| D-sphingosine | 300 | single $C_{17}$ tail |
| L-alpha-phosphatidylethanolamine (PPEA) dilauroyl | 580 | two $C_{13}$ tails |
| PPEA dimyristoyl (PPEADM) | 636 | two $C_{15}$ tails |
| PPEA dipalmitoyl (PPEADP) | 692 | two $C_{17}$ tails |
| PPEA distearoyl (PPEADS) | 748 | two $C_{19}$ tails |
| PPEA-beta-oleoyl-gamma palmitoyl | 718 | one $C_{17}$ tail, and $C_{19}$ tail with double bond |

By comparing the results given in Tables 1 to 3 above, the following conclusions can be drawn:

(a) The antigenicity of a short chain oligosaccharide (tri-saccharide: Table 1) bound with short chain spacer amines such as PPS, is low;

(b) The antigenicity of a short chain saccharide, Table 1, bound with spacer amines with double lipid tails, such as PPEADP, PPEADM, and PPEADS, is high;

(c) The antigenicity of a long chain oligosaccharide (dodecasaccharide, Table 2) is relatively strong even with short spacer amines such as PPS;

(d) The antigenicity of a long chain oligosaccharide (Table 2), bound with spacer amines with single lipid tails, such as sphingosine, is weak;

(e) The strength of binding of the neoglycolipid to the silica gel, as opposed to the antigenicity of the conjugate, (Table 3) is not of the same order as indicated for the antigenicity. For example, whereas PPEA dilauroyl binds the oligosaccharide more strongly than, for example, PPEADP (Table 3), the antigenicity of the PPEA dilauroyl complex is much lower for both tri- and dodeca-saccharides (Tables 1 and 2).

(f) The binding strength of neoglycolipids with single tails may be high (stearylamine in Table 3) but the antigenicity is low in comparison with double tailed molecules (Tables 1 and 2).

EXAMPLE 2

Materials (a) Oligosaccharides

The oligosaccharides used were: lactose, maltose, tetrasaccharide $N_1$, obtained from human meconium glycoproteins [Hounsell E. F. et al, Eur. J. Biochem 148, (1985) 367–377] and, chemically synthesised disaccharide N-acetyllactosamine, trisaccharide ($O_4$) and pentasaccharide ($O_8$) [Auge, C., David, S., and Veyrieres, A.; (1979), Nouveau J. de Chimie, 3, 491–497], and chemically synthesised 3-fucosyl-N-acetyllactosamine (3F). The synthesised saccharides were reduced with sodium borohydride. Lacto-N-fucopentaitol III (LNFP III alditol) was derived from a fraction of human milk pentasaccharides.

(b) Monoclonal Antibodies (i) human serum, Ma, containing a monoclonal anti-I antibody, at a dilution of 1:1000, and, (ii) mouse hybridoma antibody, anti-SSEA-1, at a dilution of 1:100.

(c) Lectin

The plant lectin *Ricinus communis* agglutinin, which contains a carbohydrate binding system.

Controlled Oxidation

The reduced oligosaccharides (10 micrograms) were oxidised with sodium periodate (4 equivalents) in 100 microliters of 40 mM imidazole hydrochloride (pH 6.5) at 0° C. for one hour. The resultant solutions were used immediately for combination with L-alpha-phosphatidyl-ethanolamine dipalmitoyl (PPEADP).

Combination with PPEADP

Lactose and maltose (10 micrograms) or 50 microliters of the prepared solutions of the periodate oxidised oligosaccharides were added to 150 microliters of a chloroform/methanol (1:2 v/v) solution containing 100 micrograms of PPEADP. The solutions were allowed to react at 50° C. for two hours. Sodium cyanoborohydride (50 micrograms in 10 microliters of methanol) were then added and the solutions again maintained at 50° C. for a further 116 hours. Thereafter the solvents were evaporated from the solutions under nitrogen and the residues redissolved in 40% v/v aqueous methanol. Dilutions of 10, 1.0, and 0.1 micrograms of carbohydrate per milliliter in 40% v/v aqueous methanol were prepared for PVC plate-binding assays.

Binding to Carrier Matrices (a) Binding to Plates

Aliquots of 50 microliters of the solutions of neoglycolipids, prepared as described by combination of the disaccharides, oligosaccharides with PPEADP, were added to the wells of round-bottomed flexible PVC microtiter plates. The plates were held at 4° C. for 90 minutes and then the wells were washed five times with phosphate buffered saline (PBS) of pH 7.4, and treated with a 3% w/v solution of bovine serum albumin (BSA) in PBS at 37° C. for one hour. The wells were then washed five times with PBS.

(b) Chromatographic Carrier

For chromatogram binding assays, the reduced oligosaccharide $O_4$ and lactose (3 micrograms per lane) were chromatographed on HP-TLC plates (aluminium sheets with silica gel 60 from E. Merck) using a solvent system butan-1-ol/acetone/water 6:5:4 v/v. The chromatograms were dipped into a chloroform/methanol/40 mM imidazole hydrochloride solution (pH 6.5) containing 0.02% w/v of sodium periodate and left at 4° C. for for 45 minutes and then dipped into a 1:1 v/v chloroform/methanol solution of 0.5% w/v PPEADP. They were then maintained at 60° C. for one hour and then dipped into a solution of 0.2% w/v of sodium cyanoborohydride in chloroform/methanol 1:1 v/v and incubated at 60° C. for a further two hours.

Chomatogram Binding Assay

The chromatograms were then either stained with orcinol stain or were overlaid with 5% BSA in PBS for two hours at room temperature and immunostained with anti-I(Ma) 1:100 dilution or control serum (Ns) followed by $^{125}$I-labelled anti-human IgM, as described in Uemura, K. et. al. (1983) Biosci. Reps., 3, 577–588, and autoradiographed using Singul-X RP (Trade Mark) X-ray films.

Plate-binding Immunoassay

To the wells of the prepared plates, 50 microliters of antibody preparations (dilutions 1:1000 for anti-I(Ma)-serum, and, 1:100 for anti-SSEA-1 ascites or $^{125}$I-labelled *R.communis* (60 ng containing $1 \times 10^5$ cpm in 1% BSA in PBS were added and the plates incubated at 4° C. for 16 hours. The plates were then washed five times with PBS.

For the antibody assays, $^{125}$I-labelled rabbit antibodies to human [for the anti-I (Ma) antibody] and mouse (for anti-SSEA-1) immunoglobulins were added (50 microliters containing $10^5$ cpm and 30 ng of protein per well).

For the radioassay using $^{125}$I labelled lectin, the plates were dried and the wells counted using a Nuclear Enterprises 1600 counter.

Inhibition assay procedures were adapted from Wood, E., et. al. (1979) Mol. Immunol. 16, 813–819; and Gooi, H. C., et. al; (1985) Mol. Immunol. 22, 689–693. using serial dilutions of the neoglycolipids incorporated into liposomes as inhibitors of the binding of the anti-I(Ma) ($1:10^4$ dilution) or *R. communis* lectin (30 ng containing $5 \times 10^4$ cpm) to sheep gastric mucins or meconium glycoproteins of the non-secretor type (500 ng per well). The composition of the liposomes was neoglycolipid, lecithin (dimyristoyl phosphatidyl choline) and cholesterol. Further details are discussed in Tang P. W. et al Biochem Biophys Res Comm Vol. 132, pages 474–480 (1985)

Figure 2A:
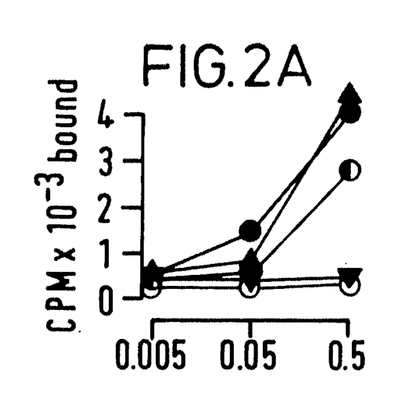

Results and Discussion (i) The anti-I(Ma) antibody bound to oligosaccharides $O_4$, $O_8$ and N, which all contain the saccharide sequence Gal-beta-1-4GlcNAc-beta-1-6-. Reference is made to FIG. 2A which shows the reactivity of anti-I(Ma) to the neoglycolipids on PVC plates. Positive binding was observed with as little as 10 to 50 ng (10 to 100 picomoles) of the oligosaccharides but no binding was detected with normal human serum or with a negative control of conjugate containing PPEADP linked to lactose.

In FIG. 2 the symbols have the following meanings:
▲ = $N_1$
● = $O_8$

Figure 2B:
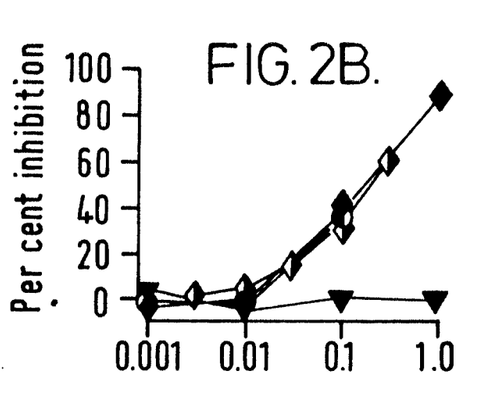
Figure 2C:
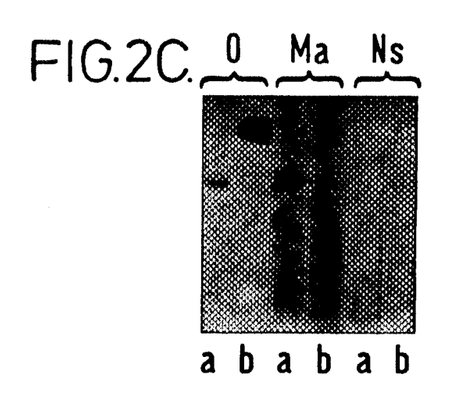
Figure 2D:
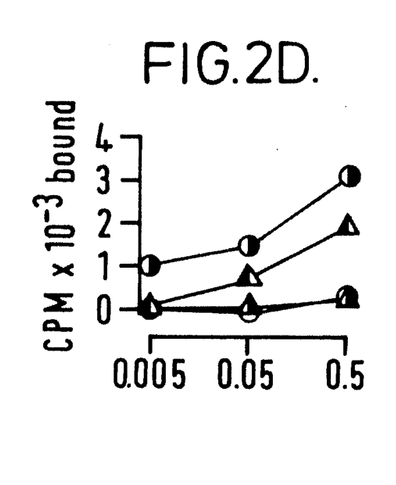

◐ = O₄
⊻ = lactose
⊕ = N-acetyllactosaminitol
◨ = maltose
◉ = LNFP III alditol
▲ = 3F
-▲ = 3F alditol
◇ = oligosaccharide alditols from sheep gastric mucins ○ = binding of neoglycolipids to control human serum (FIG. 2A) or normal mouse serum (FIG. 2D).

◆ = original (untreated sheep gastric mucins).

The abbreviation CPM stands for counts per minute.

(ii) It has previously been reported that the carbohydrate chains of sheep gastric mucins express I(Ma) as well as other antigenic determinants and that there is a 10,000-fold reduction of the antigenicity of the oligosaccharides after release from the bound peptide moiety [Wood, E., et. al., (1981) Carbohydr. Res., 90, 269–282]. FIG. 2B shows the results for inhibition-of-binding assay of anti-I(Ma) to sheep gastric mucins on PVC plates. The data indicate that when oligosaccharides derived from sheep gastric mucins are incorporated into a conjugate of this invention, using PPEADP and incorporated into liposomes, the antigenic activity of the oligosaccharide in inhibition assays is virtually indistinguishable from that of the original untreated mucin glycoprotein.

(iii) The oligosaccharide O₄, containing the I(Ma) antigen sequence produced a radioactive band on HP-TLC with immunostaining as described above, with as little as three micrograms of oligosaccharide. No immunostaining was detectable for lactose. FIG. 2C shows the results of binding of anti-I(Ma) to neoglycolipids on a TLC plate.

(iv) In PVC wells coated with the neoglycolipid obtained by reductive amination of LNFP III alditol which contains the carbohydrate sequence Gal-beta-1-4(Fuc-alpha-1-3)GlcNAc of the stage specific embryonic antigen of mouse, SSEA-1, the oligosaccharide specifically bound the hybridoma antibody, anti-SSEA-1, (FIG. 2D). The chemically synthesised trisaccharide analogue 3F, after reduction to the 3F alditol and conjugation to PPEADP, gave no binding above the control mouse serum even at the highest level (500 ng) tested. The difference may be due to the loss of one carbon unit from the N-acetylglucosamine residue of the 3F alditol during periodate oxidation, since the conjugate containing 3F without prior reduction gave substantial binding, or to a difference in orientation of the oligosaccharide moiety.

Figure 2E:
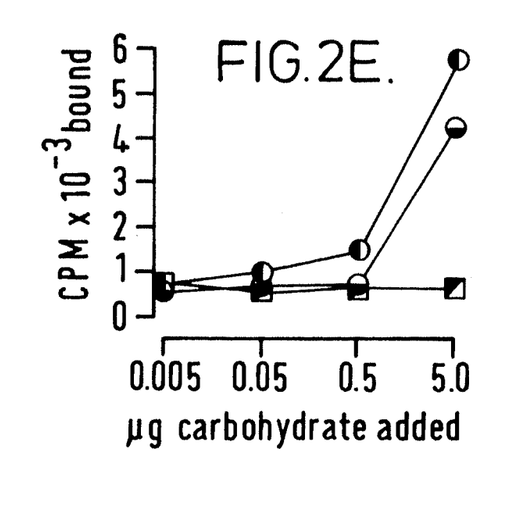

(v) Conjugates containing reduced oligosaccharide O₄ and N-acetyllactosamine were coated on to PVC plates, and shown to bind the $^{125}$I-labelled lectin *R. communis* which is known to react strongly with the sequence Gal-beta-1-4GlcNAc (FIG. 2E). A conjugate containing maltose and PPEADP gave no binding, nor did PPEADP itself.

Figure 2F:
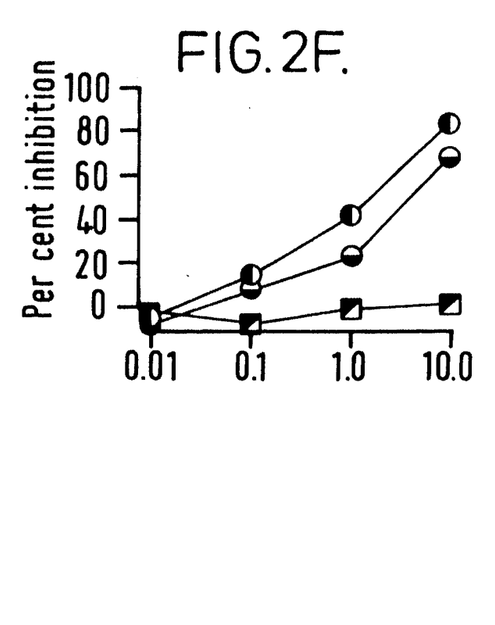

(vi) The conjugates containing the oligosaccharide O₄ and N-acetyllactosamine were incorporated into liposomes and were shown to inhibit specifically binding of the lectin to human meconium glycoproteins (FIG. 2F).

EXAMPLE 3

Reduced O-linked and reducing N-linked oligosaccharide chains were obtained from galactosyltransferase, an enzyme from human milk, by alkaline borohydride degradation and hydrazinolysis and purified by ion-exchange chromatography. Three preparations of the enzyme were used: (1) combined galactosyltransferase from donors of unknown blood group; (2) combined milk from blood group A donors; and, (3) milk from a single donor of blood group O (non-secretor). For deglycosylation an aliquot of galactosyltransferase preparation 3 was treated with anhydrous hydrogen fluoride for one hour at 4° C. The mixture was extensively dialysed against water then lyophilised and the residue redissolved in isotonic saline.

Galactosyltransferase (600 micrograms of preparations 1 and 3 or 300 micrograms of preparation 2) containing 5% of hexose as determined by phenol sulphuric acid assay using preparation 3, was treated with 0.05M NaOH/M NaBH₄ (200 microliters) at 50° C. for 24 hours to release the O-linked oligosaccharides. After acidification with acetic acid to pH 5.0 the mixture (250 microliters) was applied to a column (0.4×1 cm) of Dowex AG50W-X8 (Trade Mark) (H+) resin (200–400 mesh). Elution with water (1.2 ml) gave the O-linked oligosaccharide fraction. The fraction was evaporated to dryness at 60° C. in vacuo and methanol (200 microliters) was thrice evaporated from the residue to remove boric acid.

Elution with 3M ammonium hydroxide (1.2 ml) yielded the peptides and glycopeptides with the N-linked oligosaccharides. This fraction was evaporated to dryness at 60° C. in vacuo and water (500 microliters) was evaporated from the residue which was then subjected to hydazinolysis and N-acetylation. The products (250 microliters) were chromatographed on the same resin as described above. The unretained fraction contained the N-linked oligosaccharides. Fractions corresponding to the O- and N-linked oligosaccharides were also obtained from preparation 3 which had been deglycosylated as described above.

The oligosaccharides were resolved by HP-TLC on silica gel 60 (Merck 5641, Trade Mark) using butan-1-ol:acetone:water, 6:5:4, and visualised with 0.2% orcinol in 2M ethanolic sulphuric acid.

For antibody binding assays on PVC plates and inhibition-of-binding assays, reduced O-linked fractions released from galactosyltransferase (100–600 micrograms) were dried at 60° C. in vacuo and oxidised with sodium periodate (10–60 micrograms as appropriate) in 40 mM imidazole hydrochloride (pH 6.5, 100 microliters) at 0° C. for 45 minutes. To the resulting mixtures, chloroform/methanol (1:1) was added (240–480 microliters as appropriate) containing PPEADP (240–480 micrograms) and NaCNBH₃ (100–200 micrograms) and the mixtures incubated at 50° C. for 16 hours. The reducing oligosaccaharides released by hydrazinolysis of galactosyltransferase (100 to 600 micrograms) were coupled to PPEADP without periodate oxidation. The entire reaction mixtures were used for antibody binding on PVC plates and inhibition-of-binding assays.

For chromatogram binding assays, O-linked oligosaccharides from 15 micrograms of galactosyltransferase (preparation 1) were subjected to HP-TLC, oxidised with periodate in situ and coupled to PPEADP as described in Example 2. N-linked oligosaccharides from 15 micrograms of galactosyltransferase were chromatographed and coupled to PPEADP without periodate oxidation.

EXAMPLE 4

Immunochemical and chromatographic studies were carried out, using the procedures described in Example 2, on keratan sulphate proteoglycans which express antigenic determinants recognised by several monoclonal antibodies.

Ten sulphated oligosaccharides were purified from bovine corneal keratan sulphate after endo-beta-galactosidase digestion according to the procedure described in Scudder et al, Eur. J. Biochem. 157, 365–373 (1986).

The oligosaccharides were converted to neoglycolipids with PPEADP. For chromatographic studies, the conversion was carried out in situ.

When bound to PVC plates or to the chromatographic support, it was possible to effect a variety of immunological tests on the oligosaccharides which in this immobilised form were presented in spatial configuration which permitted antibody binding.

The results of this work are reported in Eur. J. Biochem. (1986) 157, 385–391 and *Eur. J. Biochem.* 160, 537–545.

We claim:

1. An immobilized biochemical reagent comprising (a) a solid immobilizing carrier having bound thereon (b) a conjugate which is a reaction product of (1) an oligosaccharide and (2) a lipid spacer molecule having at least two hydrophobic chains, whereby the oligosaccharide is held in spaced relationship to said solid immobilizing carrier by said lipid spacer molecule and is presented in antigenically active steric configuration for binding on encountering an antibody.

2. The reagent as claimed in claim 1, wherein said hydrophobic chains comprise linear alkyl groups containing from 5 to 50 carbon atoms.

3. The reagent as claimed in claim 1, in which said oligosaccharide and said lipid form a neoglycolipid in which the neoglycolipid has the general formula:

wherein $R^1$ represents a carbohydrate group derived from said oligosaccharide, $R^2$ represents an alkyl or alkoyl group, $R^3$ represents an alkyl or alkoyl group, $R^4$ represents an alkyl or alkoyl group, or hydrogen, $R^2$, $R^3$ and $R^4$ being the same or different groups, X represents a linking group selected from the group consisting of:

and and z is zero or 1, 2 or 3.

4. The reagent as claimed in claim 3 in which the group X is a residue of a compound selected from the group consisting of phosphatidyl ethanolamine dipalmitoyl (PPEADP), L-alpha-phosphatidyl-L-serine, L-alpha-phosphatidyl-ethanolamine (PPEA) dilauroyl, PPEA dimyristoyl, PPEA distearoyl, and PPEA beta-oleoyl-gamma-palmitoyl.

5. The reagent as claimed in claim 4 in which the oligosaccharide is derived from a glycoprotein or proteoglycan.

6. The reagent as claimed in claim 4 in which the solid immobilizing carrier is selected from the group consisting of a chromatographic support material, and a plate of plastics material.

7. The reagent as claimed in claim 6 in which the plastics material is polyvinyl chloride.

8. The reagent as claimed in claim 6 in which the chromatographic support material is silica gel.

9. The reagent as claimed in claim 3, wherein each of $R^2$, $R^3$ and $R^4$ independently of the others represents a linear $C_5$ to $C_{50}$ alkyl group or a linear ($C_5$ to $C_{50}$ alkyl) carbonyl group.

10. The reagent as claimed in claim 9, wherein each of $R^2$, $R^3$ and $R^4$ independently of the others represents a linear $C_{10}$ to $C_{25}$ alkyl group or a linear ($C_{10}$ to $C_{25}$ alkyl) carbonyl group.

11. The reagent as claimed in claim 1 or 3 in which the oligosaccharide is derived from a glycoprotein or proteoglycan.

12. The reagent as claimed in claim 1 or 3 in which the solid immobilizing carrier is selected from the group consisting of a chromatographic support material, and a plate of plastics material.

13. A biochemical assay kit comprising (1) an immobilized biochemical reagent as claimed in any one of claim 1, 3, 4, 5 or 6 in which said solid immobilizing carrier is a test plate and (2) at least one further reagent selected from a solution of a neoglycolipid of which the glyco group is the said oligosaccharide and a solution of liposome-forming components.

14. A biochemical assay kit comprising (1) an immobilized biochemical reagent as claimed in claim 11 in which said solid immobilizing carrier is a test plate, (2) a reagent comprising a solution of a neoglycolipid of which the glyco group is the said oligosaccharide and (3) a further reagent comprising a solution of liposome-forming components.

15. A biochemical assay kit comprising (1) an immobilized biochemical reagent as claimed in claim 12 in which said solid immobilizing carrier is a test plate, (2) a reagent comprising a solution of a neoglycolipid of which the glyco group is the said oligosaccharide and (3) a further reagent comprising a solution of liposome-forming components.

16. A method of preparing an immobilized biochemical reagent, comprising reacting a reducing oligosaccharide containing a reactive aldehyde group and an amine derivative of a lipid having at least two hydrophobic chains to produce a neoglycolipid and bonding the reaction product to a solid immobilizing carrier.

17. The method as claimed in claim 16, wherein said hydrophobic chains comprise linear alkyl groups containing from 5 to 50 carbon atoms.

18. The method as claimed in claim 16, wherein said hydrophobic chains are selected from linear $C_{10}$ to $C_{25}$ alkyl groups and linear ($C_{10}$ to $C_{25}$ alkyl) carbonyl groups.

19. The method of preparing an immobilized biochemical reagent as claimed in claim 16 wherein said oligosaccharide is an oligosaccharide liberated from an immunogenic glycoprotein or proteoglycan.

20. The method of preparing an immobilized biochemical reagent as claim in claim 19 wherein said oligosaccharide is liberated by contacting said glycoprotein or said proteoglycan with an enzyme.

21. The method of preparing an immobilized biochemical reagent as claimed in claim 19 wherein said oligosaccharide is liberated by contacting said glycoprotein or said proteoglycan with alkaline borohydride, followed by oxidizing said liberated oligosaccharide with periodate to form an aldehyde group thereon.

22. The method of preparing an immobilized biochemical reagent as claimed in claim 19 wherein said oligosaccharide is liberated by contacting said glycoprotein or said proteoglycan with hydrazine, followed by re-N-acylation to form a re-N-acylated oligosaccharide.

23. The method of preparing an immobilized biochemical reagent as claimed in claim 22 wherein said amine derivative of said lipid and said re-N-acylated oligosaccharide are reacted in the presence of cyanoborohydride to form a neoglycolipid.

24. The method as claimed in claim 22, wherein said re-N-acylated oligosaccharide is reacted with sodium borohydride to cleave the terminal saccharide ring structure with formation of a methylol group and then with periodate to form a reducing aldehyde group for reaction with an amine group on the lipid derivative.

25. A method of conducting a biochemical assay, comprising providing an immobilized biochemical reagent comprising (a) a solid immobilizing carrier having bound thereon (b) a conjugate which is a reaction product of (1) an oligosaccharide and (2) a lipid spacer molecule having at least two hydrocarbon chains, whereby the oligosaccharide is held in spaced relationship to said solid immobilizing carrier by said lipid spacer molecule and is presented in antigenically active steric configuration for binding on encountering an antibody; (3) contacting said conjugate with an antibody to the oligosaccharide to form an antibody-conjugate complex whereby the antibody binds to the oligosaccharide of said conjugate; and (4) detecting said complex with an analytically detectable reagent.

26. The method as claimed in claim 25, wherein said hydrophobic chains comprise linear alkyl groups containing from 5 to 50 carbon atoms.

27. The method as claimed in claim 25, wherein said hydrophobic chains are selected from linear $C_{10}$ to $C_{25}$ alkyl groups and linear ($C_1$ to $C_{25}$ alkyl) carbonyl groups.

28. The method of conducting a biochemical assay as claimed in claim 25, which includes an inhibition assay step comprising contacting said complex with a second biochemical reagent comprising a conjugate of an oligosaccharide with a solid phase or a liposome carrier.

29. The method of conducting a biochemical assay as claimed in claim 25, wherein the analytically detectable reagent is a radiolabelled antibody to the bound antibody.

30. The method as claimed in claim 29, wherein detection of said radiolabelled antibody is effected by autoradiography.

31. An immobilized biochemical reagent comprising (a) a solid immobilizing carrier having bound therein (b) a conjugate which is a reaction product of (1) an oligosaccharide selected from the group consisting of monosaccharides and oligosaccharides containing up to 12 saccharide residues, and (2) a lipid spacer molecule having at least two hydrophobic chains, whereby the oligosaccharide is held in spaced relationship to said solid immobilizing carrier by said lipid spacer molecule and is presented in antigenically active steric configuration for binding on encountering an antibody.

32. The reagent as claimed in claim 31, wherein said hydrophobic chains comprise linear alkyl groups containing from 5 to 50 carbon atoms.

33. The reagent as claimed in claim 31 in which the oligosaccharide is derived from a glycoprotein or proteoglycan.

34. The reagent as claim in claim 31 in which said oligosaccharide and said lipid form a neoglycolipid in which the neoglycolipid has the general formula:

wherein $R^1$ represents a carbohydrate group derived from said oligosaccharide, $R^2$ represents an alkyl or alkoyl group, $R^3$ represents an alkyl or alkoyl group, $R^4$ represents an alkyl or alkoyl group, or hydrogen, $R^2$, $R^3$, and $R^4$ being the same or different groups, and X represents a linking group selected from the group consisting of:

and z is zero or 1, 2 or 3.

35. The reagent as claimed in claim 34, wherein each of $R^2$, $R^3$ and $R^4$ independently of the others represents a linear $C_5$ to $C_{50}$ alkyl group or a linear ($C_5$ to $C_{50}$ alkyl) carbonyl group.

36. The reagent as claimed in claim 35, wherein each of $R^2$, $R^3$ and $R^4$ independently of the others represents a linear $C_{10}$ to $C_{25}$ alkyl group or a linear ($C_{10}$ to $C_{25}$ alkyl) carbonyl group.

37. The reagent as claimed in claim 34, in which the group X is a residue of a compound selected from the group consisting of phosphatidyl ethanolamine dipalmitoyl (PPEADP), L-alpha-phosphatidyl-L-serine, L-alpha-phosphatidyl-ethanolamine (PPEA) dilauroyl, PPEA dimyristoyl, PPEA distearoyl, and PPEA beta-oleoyl-gamma-palmitoyl.

38. The reagent as claim in claim 37 in which the solid immobilizing carrier is selected from the group consisting of a chromatographic support material and a plate of plastics material.

39. The reagent as claimed in claim 38 in which the plastics material is polyvinyl chloride.

40. The reagent as claimed in claim 38 in which the chromatographic support material is silica gel.

41. The reagent as claimed in claim 31 or 34 in which the oligosaccharide is derived from a glycoprotein or proteoglycan.

42. The reagent as claimed in claim 31 or 34, in which the solid immobilizing carrier is selected from the group consisting of a chromatographic support material and a plate of plastics material.

43. A biochemical assay kit comprising (1) an immobilized biochemical reagent as claimed in claim 41, in which said solid immobilizing carrier is a test plate (2) a reagent comprising solution of neoglycolipid of which the glyco group is the said oligosaccharide and (3) a further reagent comprising a solution of liposome-forming components.

44. A biochemical assay kit comprising (1) an immobilized biochemical reagent as claimed in claim 42, in which said solid immobilizing carrier is a test plate, (2) a reagent comprising solution of a neoglycolipid of which the glyco groups is the said oligosaccharide and (3) a further reagent comprising a solution of liposome-forming components.

45. A biochemical assay kit comprising (1) an immobilized biochemical reagent as claimed in any one of claims 31, 34, 37, 33 or 38, in which said solid immobilizing carrier is a test plate and (2) at least one further reagent selected from a solution of neoglycolipid of which the glyco group is the said oligosaccharide and a solution of liposome-forming components.

46. A method of preparing an immobilized biochemical reagent comprising reacting a reducing oligosaccharide, which contains an aldehyde group and which is selected from the group consisting of monosaccharides and oligosaccharides containing up to 12 saccharide residues, and an amine derivative of a lipid having at least two hydrophobic chains to produce a neoglycolipid, and bonding the reaction product to a solid immobilizing carrier whereby the oligosaccharide is held in spaced relationship to said solid immobilizing carrier by said lipid.

47. The method of preparing an immobilized biochemical reagent as claimed in claim 46 wherein said oligosaccharide is an oligosaccharide liberated from an immunogenic glycoprotein or proteoglycan.

48. The method of preparing an immobilized biochemical reagent as claimed in claim 47 wherein said oligosaccharide is liberated by contacting said glycoprotein or said proteoglycan with an enzyme.

49. The method of preparing an immobilized biochemical reagent as claimed in claim 47 wherein said oligosaccharide is liberated by contacting said glycoprotein or said proteoglycan with alkaline borohydride, followed by oxidizing said liberated oligosaccharide with periodate to form an aldehyde group thereon.

50. The method of preparing an immobilized biochemical reagent as claimed in claim 47, wherein said oligosaccharide is liberated by contacting said glycoprotein or said proteoglycan with hydrazine, followed by re-N-acylation to form a re-N-acylated oligosaccharide.

51. The method of preparing an immobilized biochemical reagent as claimed in claim 50, wherein said re-N-acylated oligosaccharide is reacted with sodium borohydride to cleave the terminal saccharide ring structure with formation of a methylol group and then with periodate to form a reducing aldehyde group for reaction with an amine group on the lipid derivative.

52. The method of preparing an immobilized biochemical reagent as claimed in claim 50 wherein said amine derivative of said lipid and said re-N-acylated oligosaccharide are reacted in the presence of cyanoborohydride to form a neoglycolipid.

53. A method of conducting a biochemical assay, comprising providing an immobilized biochemical reagent comprising (a) a solid immobilizing carrier having bound thereon (b) a conjugate which is a reaction product of (1) an oligosaccharide selected from the group consisting of monosaccharides and oligosaccharides containing up to 12 saccharide residues, and (2) a lipid spacer molecule having at least two hydrophobic chains, whereby the oligosaccharide is held in spaced relationship to said solid immobilizing carrier by said lipid spacer molecule and is presented in antigenically active steric configuration for binding on encountering an antibody; contacting said conjugate with an antibody to the oligosaccharide to form an antibody-conjugate complex whereby the antibody binds to the oligosaccharide of said conjugate; and detecting said complex with an analytically detectable reagent.

54. The method of conducting a biochemical assay as claimed in claim 53 which includes an inhibition assay step comprising contacting said complex with a second biochemical reagent comprising a conjugate of an oligosaccharide with a solid phase or a liposome carrier.

55. The method of conducting a biochemical assay as claimed in claim 53, wherein the analytically detectable reagent is a radiolabelled antibody to the bound antibody.

56. The method of conducting a biochemical assay as claimed in claim 53, wherein detection of said radiolabelled antibody is effected by autoradiography.

* * * * *